US010856969B2

(12) United States Patent
Ishikawa

(10) Patent No.: US 10,856,969 B2
(45) Date of Patent: Dec. 8, 2020

(54) TORIC INTRAOCULAR LENS AND INTRAOCULAR LENS INSERTION APPARATUS

(71) Applicant: Kowa Company, Ltd., Nagoya (JP)

(72) Inventor: Haruo Ishikawa, Nagoya (JP)

(73) Assignee: KOWA COMPANY, LTD., Nagoya (JP)

(*) Notice: Subject to any disclaimer, the term of this patent is extended or adjusted under 35 U.S.C. 154(b) by 254 days.

(21) Appl. No.: 16/092,188

(22) PCT Filed: Apr. 7, 2017

(86) PCT No.: PCT/JP2017/014485
§ 371 (c)(1),
(2) Date: Oct. 8, 2018

(87) PCT Pub. No.: WO2017/175853
PCT Pub. Date: Oct. 12, 2017

(65) Prior Publication Data
US 2019/0091008 A1    Mar. 28, 2019

(30) Foreign Application Priority Data
Apr. 8, 2016 (JP) ................................. 2016-078333

(51) Int. Cl.
*A61F 2/16* (2006.01)

(52) U.S. Cl.
CPC .............. *A61F 2/167* (2013.01); *A61F 2/16* (2013.01); *A61F 2/1645* (2015.04);
(Continued)

(58) Field of Classification Search
CPC ........ A61F 2/16; A61F 2/1613; A61F 2/1645; A61F 2/1648; A61F 2/1662; A61F 2/167;
(Continued)

(56) References Cited

U.S. PATENT DOCUMENTS 5,092,880 A      3/1992   Ohmi
5,800,532 A  *   9/1998   Lieberman ............ A61F 2/1618
                                                        351/159.08
(Continued)

FOREIGN PATENT DOCUMENTS

EP      2343029 A1      7/2011
JP      2014-073211 A   4/2014
(Continued)

OTHER PUBLICATIONS

European Search Report issued in European patent application No. 17779231.4, dated Oct. 22, 2019.
(Continued)

*Primary Examiner* — Ryan J. Severson
(74) *Attorney, Agent, or Firm* — Knobbe, Martens, Olson & Bear LLP

(57) ABSTRACT

A toric intraocular lens includes a lens body, support portions, and connecting portions for connecting the lens body and the support portions. The lens is housed in an insertion apparatus that includes a tubular apparatus body having an insertion tube for the lens and a plunger for moving the lens. Each of the connecting portions is arranged at a position where the connecting portions face each other across a center of an optical axis of the lens body. One end of the flat meridian of the lens body is located at a position opposite to a position, with respect to an axis that passes through the center and connects the connecting portions, at which the plunger contacts the lens body. An angle between the flat meridian and an axis along which the lens is pushed by the plunger is larger than 0° and equal to or smaller than 90°.

8 Claims, 12 Drawing Sheets

(52) U.S. Cl.
CPC .... *A61F 2/1672* (2013.01); *A61F 2002/1686* (2013.01); *A61F 2250/0096* (2013.01)

(58) Field of Classification Search
CPC ................. A61F 2/1672; A61F 2/1678; A61F 2002/1681; A61F 2002/169
See application file for complete search history.

(56) References Cited

U.S. PATENT DOCUMENTS

| | | | | |
|---|---|---|---|---|
| 8,256,896 | B2* | 9/2012 | Zhao | A61F 2/1637 351/159.72 |
| 8,357,196 | B2* | 1/2013 | Jain | A61F 2/16 623/6.11 |
| 8,465,543 | B2* | 6/2013 | Fiala | A61F 2/1645 623/6.23 |
| 8,521,318 | B2* | 8/2013 | Zhao | A61F 2/1645 700/117 |
| 9,364,316 | B1* | 6/2016 | Kahook | A61F 2/1648 |
| 9,421,088 | B1* | 8/2016 | Kahook | A61F 2/1648 |
| 9,782,254 | B2* | 10/2017 | Perera | A61F 2/167 |
| 9,925,040 | B2* | 3/2018 | Kahook | A61F 2/1613 |
| 9,925,041 | B2* | 3/2018 | Gerlach | A61F 2/1654 |
| 10,010,409 | B2* | 7/2018 | Attinger | A61F 2/1672 |
| 10,394,051 | B2* | 8/2019 | Ben-Yaish | G02C 7/04 |
| 10,426,602 | B2* | 10/2019 | Tseng | A61F 2/1691 |
| 2010/0079723 | A1* | 4/2010 | Kingston | A61F 2/1613 351/159.54 |
| 2010/0315589 | A1* | 12/2010 | Portney | A61F 2/1645 351/159.21 |
| 2011/0118836 | A1* | 5/2011 | Jain | A61F 2/16 623/6.27 |
| 2011/0205486 | A1* | 8/2011 | Zhao | A61F 2/1637 351/159.21 |
| 2013/0060542 | A1* | 3/2013 | Zhao | A61F 2/1637 703/2 |
| 2014/0022508 | A1* | 1/2014 | Ben-Yaish | G02C 7/042 351/159.38 |
| 2014/0121767 | A1* | 5/2014 | Simpson | A61F 2/1637 623/6.23 |
| 2016/0000556 | A1* | 1/2016 | Perera | A61F 2/167 606/107 |
| 2016/0157997 | A1* | 6/2016 | Gerlach | A61F 2/1637 623/6.25 |
| 2016/0250020 | A1* | 9/2016 | Kahook | A61F 2/1613 623/6.46 |
| 2016/0270907 | A1* | 9/2016 | Attinger | A61F 2/1672 |
| 2016/0331519 | A1* | 11/2016 | Kahook | A61F 2/167 |
| 2017/0304047 | A1* | 10/2017 | Argal | A61F 2/1654 |
| 2018/0161153 | A1* | 6/2018 | Kahook | A61F 2/1648 |
| 2018/0200105 | A1* | 7/2018 | Nguyen | A61F 2/1678 |
| 2019/0091008 | A1* | 3/2019 | Ishikawa | A61F 2/16 |
| 2019/0105151 | A1* | 4/2019 | Tseng | A61F 2/1678 |
| 2019/0167416 | A1* | 6/2019 | Ishikawa | A61F 2/1645 |
| 2019/0262127 | A1* | 8/2019 | Demas | A61F 2/1618 |
| 2019/0374334 | A1* | 12/2019 | Brady | A61F 2/1618 |
| 2020/0008931 | A1* | 1/2020 | Argento | A61F 2/1645 |
| 2020/0081268 | A1* | 3/2020 | Ben-Yaish | G02C 7/042 |

FOREIGN PATENT DOCUMENTS

| | | |
|---|---|---|
| JP | 5771907 B2 | 9/2015 |
| WO | WO 2015/037994 A1 | 3/2015 |

OTHER PUBLICATIONS

International Search Report received in PCT/JP2017/014485 dated Jul. 4, 2017.

* cited by examiner

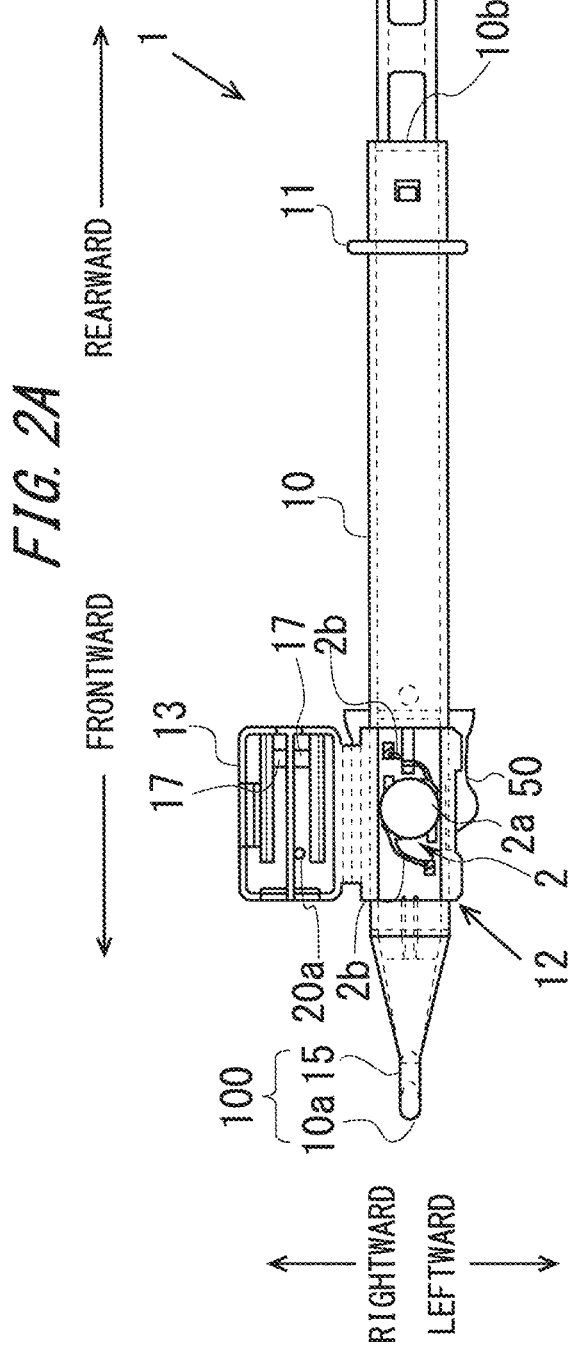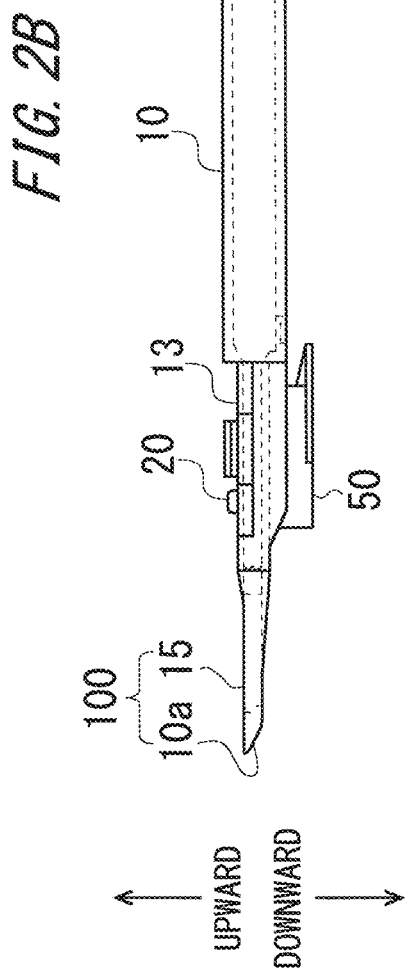
FIG. 2A
FIG. 2B

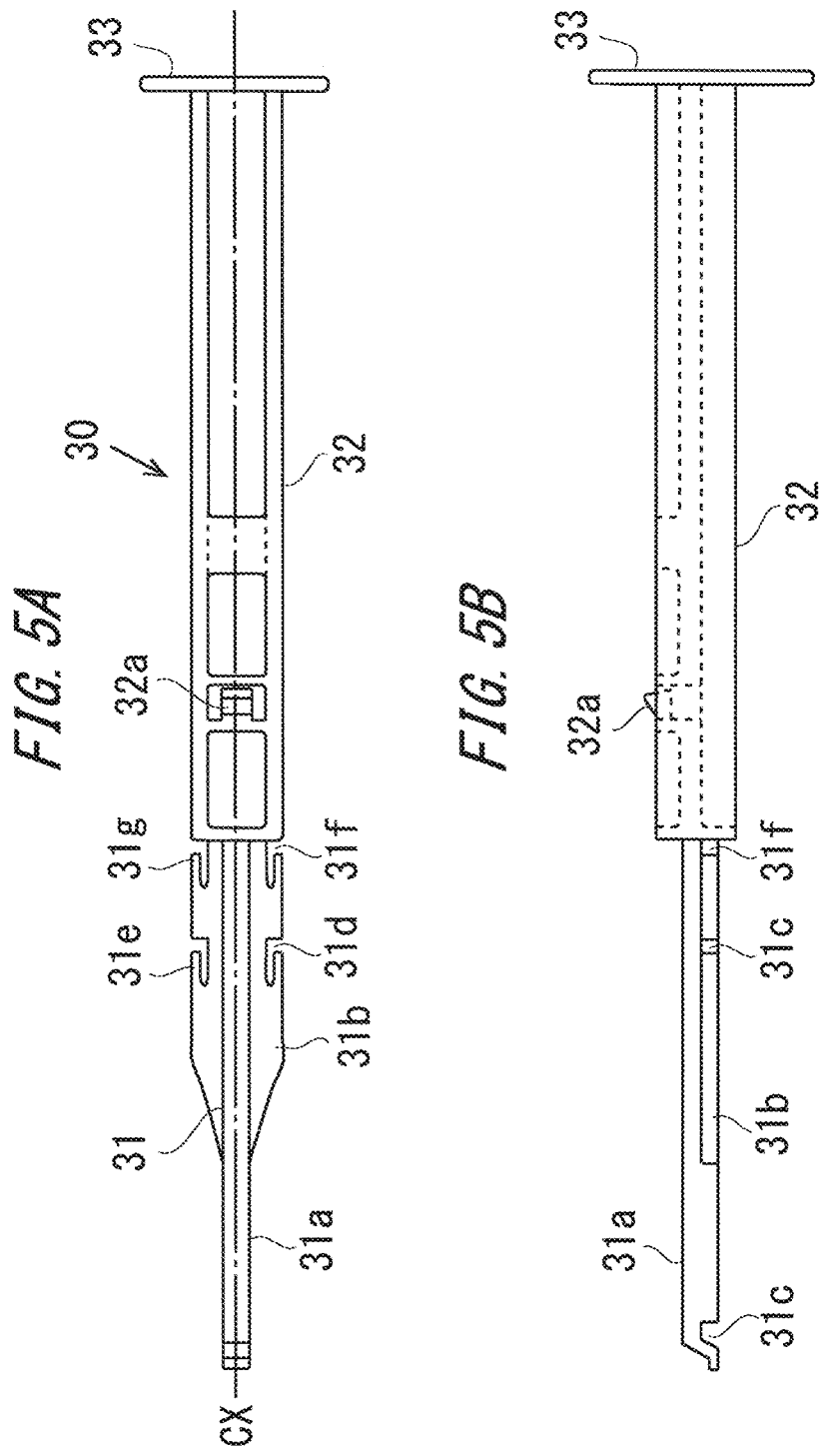

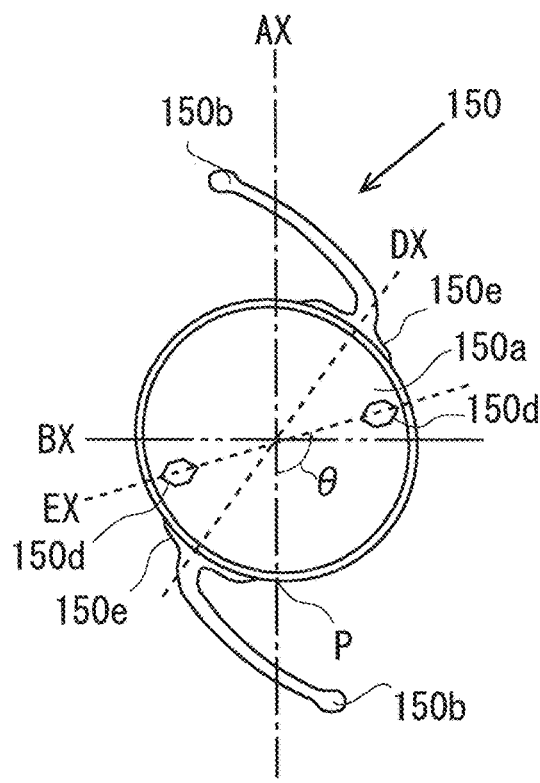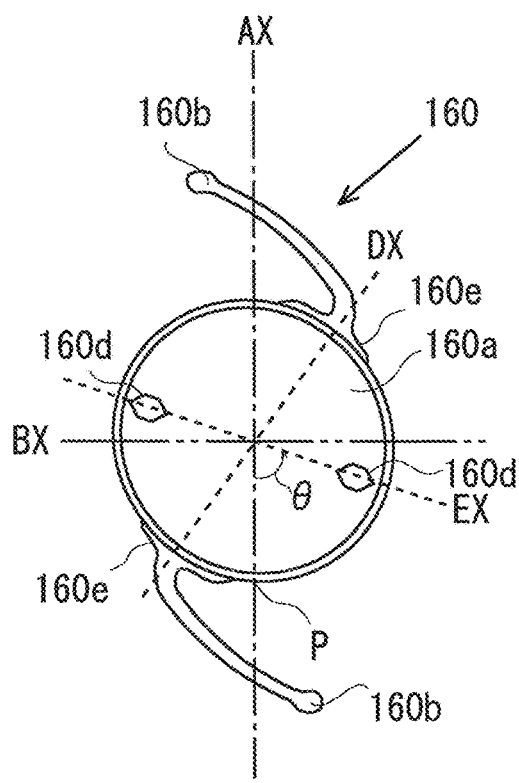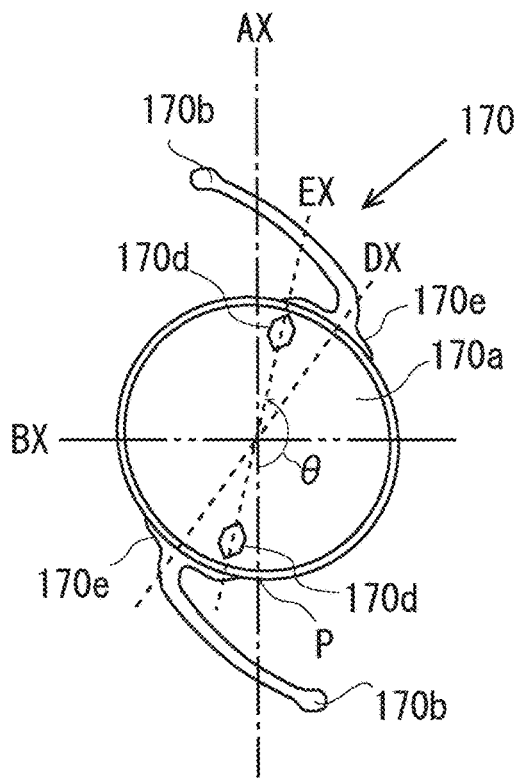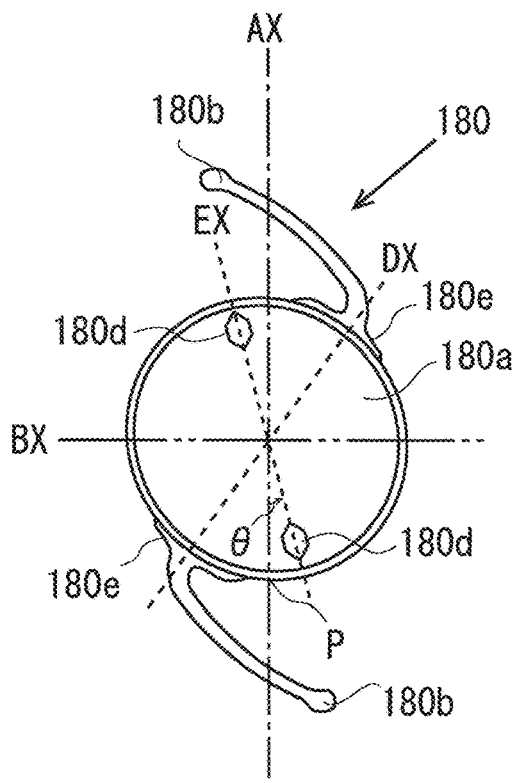

*FIG. 9*

| LENS | AXIS SHIFT |
|---|---|
| 110 | OCCUR |
| 120 | NONE |
| 130 | NONE |
| 140 | OCCUR |
| 150 | OCCUR |
| 160 | NONE |
| 170 | OCCUR |
| 180 | NONE |

TORIC INTRAOCULAR LENS AND INTRAOCULAR LENS INSERTION APPARATUS

FIELD OF THE INVENTION

The embodiments discussed herein relate to a toric intraocular lens and an intraocular lens insertion apparatus.

BACKGROUND

Intraocular lenses are widely used to replace opaque crystalline lenses of human eyes and to compensate the refraction of the lenses in cataract treatments. In an intraocular lens insertion surgery for a patient with corneal astigmatism, an intraocular lens that is capable of correcting the astigmatism, what is called a toric intraocular lens, may be inserted into an eyeball of the patient. When the toric intraocular lens is inserted into the eyeball of the patient, the toric axis of the intraocular lens needs to be matched with the astigmatism axis of the cornea of the patient.

Conventionally, a toric intraocular lens is provided with a mark for indicating the toric axis. The toric intraocular lens includes a lens body having a predetermined refractive power and support portions that are connected to the lens body and are provided for holding the lens body inside of the eyeball. The mark for indicating the toric axis is provided for the lens body near a connecting portion that connects with the support portion. Alternatively, since it is assumed that an intraocular lens insertion apparatus is used to push the toric intraocular lens into the eyeball, the lens body and the support portions of the toric intraocular lens may be configured such that the push direction of the toric intraocular lens is parallel with the flat meridian of the toric intraocular lens when the toric intraocular lens is pushed by the intraocular lens insertion apparatus (See Patent Literature 1, for example).

In a case of what is called one-piece type toric intraocular lens, in which the lens body and the support portions of the toric intraocular lens are made of the same material, the thickness of the connecting portion that connects the lens body with the support portion tends to be larger than the thicknesses of other portions of the lens in order to enhance the strength of the support portion. In this case, since the opening for ejecting the toric intraocular lens is configured to be relatively small in the intraocular lens insertion apparatus, it is needed that the thick connecting portion does not interfere with the movement of the toric intraocular lens in the intraocular lens insertion apparatus. Therefore, the relative positions of the lens body and the support portions need to be determined such that the positions of the support portions of the toric intraocular lens relative to the push direction thereof are appropriate. In addition, the cross section area of the lens body of the toric intraocular lens in the direction of the optical axis in the flat meridian direction differs from the cross section area thereof in the steep meridian direction, and the thickness of the lens body in the flat meridian direction is larger than the thickness of the lens body in the steep meridian direction. Thus, the relative positions of the flat meridian direction and the steep meridian direction relative to the push direction of the toric intraocular lens also need to be determined such that the relative positions do not interfere with the movement of the toric intraocular lens in the intraocular lens insertion apparatus.

CITATION LIST

Patent Literature

[PTL 1] JP-B-5771907

SUMMARY OF THE INVENTION

Technical Problem

However, in the toric intraocular lens as described above, providing the mark for indicating the toric axis near the connecting portion that connects the lens body with the support portion means that the connecting portion connects with the flat meridian portion of the lens body. That is, since the thick connecting portion connects with the flat meridian portion, the thickness of the entire toric intraocular lens becomes off-balance. When a toric intraocular lens is configured such that the bias of the thickness (in the flat meridian direction, in this case) exists, a stable push of the toric intraocular lens may be interfered because the tip of the toric intraocular lens push member (plunger) of the intraocular lens insertion apparatus may behave like escaping toward a thinner portion of the toric intraocular lens when the plunger pushes the toric intraocular lens.

In addition, even when the push direction of the toric intraocular lens by the intraocular lens insertion apparatus and the flat meridian direction of the lens body of the toric intraocular lens are configured to be parallel with each other and the plunger is configured such that the tip of the plunger contacts the thicker portion of the lens body of the toric intraocular lens, the portion of the lens body other than the portion in the flat meridian direction becomes thinner than the portion in the flat meridian direction. Again, a stable push of the toric intraocular lens may be interfered because the tip of the plunger may behave like escaping toward a portion of the toric intraocular lens other than the portion in the flat meridian direction when the plunger pushes the toric intraocular lens.

The technique of this disclosure has been made in view of the above-mentioned circumstances, and it is an object of this disclosure to provide a toric intraocular lens which achieves a more stable push of the toric intraocular lens by the intraocular lens insertion apparatus.

Solution to Problem

According to the embodiments described herein, it is provided a toric intraocular lens including a lens body having a flat meridian and a steep meridian, a pair of support portions for positioning the lens body in an eyeball, and connecting portions for connecting the lens body and the support portions. The toric intraocular lens is housed in an intraocular lens insertion apparatus that includes a tubular apparatus body having an insertion tube at a distal end of the apparatus body for inserting the toric intraocular lens into the eyeball and a plunger for moving the toric intraocular lens to a distal end of the insertion tube. Each of the connecting portions is arranged at a position where the connecting portions face each other across a center of an optical axis of the lens body. One end of the flat meridian of the lens body is located at a position opposite to a position, with respect to an axis that passes through the center of the optical axis and connects the connecting portions with each other, at which a tip of the plunger contacts a circumference of the lens body. An angle θ between the flat meridian of the lens body and an axis of the plunger along which the toric intraocular lens is pushed by the plunger is larger than 0° and equal to or smaller than 90°. With such a configuration, since the tip of the plunger contacts a thinner portion of the lens body, an axis shift that may occur when the plunger pushes the toric intraocular lens can be preferably prevented.

Preferably, the above toric intraocular lens can be configured such that when the tip of the plunger contacts the circumference of the lens body, the angle θ is equal to or larger than an angle that achieves that a line extending the flat meridian does not intersect the plunger and equal to or smaller than 90°. Alternatively, the above toric intraocular lens can be configured such that the angle θ is larger than 10° and smaller than 80°. Alternatively, the above toric intraocular lens can be configured such that the angle θ is substantially equal to 45°. In addition, the above toric intraocular lens can be configured such that a mark is provided for each end of the flat meridian on the lens body. Further, the above toric intraocular lens can be configured such that a tip of the support portion is located on an axis that connects the marks with each other. More preferably, the above toric intraocular lens can be configured such that an angle between the axis that connects the connecting portions with each other and the flat meridian is from 45°−10° to 45°+10°. In addition, the toric intraocular lens can be housed in advance in a housing member for housing the toric intraocular lens of the intraocular lens insertion apparatus.

Advantageous Effects of Invention

According to the technique disclosed herein, it is possible to provide a toric intraocular lens which achieves a more stable push of the toric intraocular lens by the intraocular lens insertion apparatus.

BRIEF DESCRIPTION OF THE DRAWINGS

FIG. 2A is a diagram schematically illustrating a configuration of an intraocular lens insertion apparatus according to one embodiment.

FIG. 2B is another diagram schematically illustrating a configuration of an intraocular lens insertion apparatus according to one embodiment.

FIG. 5A is a diagram schematically illustrating a configuration of a plunger according to one embodiment.

FIG. 5B is another diagram schematically illustrating a configuration of a plunger according to one embodiment.

FIG. 7A is a diagram schematically illustrating a configuration of a toric intraocular lens in another case where an axis shift of a plunger occurs and in another case where the axis shift of the plunger does not occur.

FIG. 7B is another diagram schematically illustrating a configuration of a toric intraocular lens in another case where an axis shift of a plunger occurs and in another case where the axis shift of the plunger does not occur.

FIG. 7C is yet another diagram schematically illustrating a configuration of a toric intraocular lens in another case where an axis shift of a plunger occurs and in another case where the axis shift of the plunger does not occur.

FIG. 7D is further another diagram schematically illustrating a configuration of a toric intraocular lens in another case where an axis shift of a plunger occurs and in another case where the axis shift of the plunger does not occur.

FIG. 9 is a table illustrating a verification result of whether an axis shift of a plunger occurs when the plunger pushes the toric intraocular lens as illustrated in FIGS. 6A to 6D and FIGS. 7A to 7D.

DETAILED DESCRIPTION OF THE PREFERRED EMBODIMENTS

Hereinafter, embodiments of the present invention are described with reference to drawings.

Figure 1A:
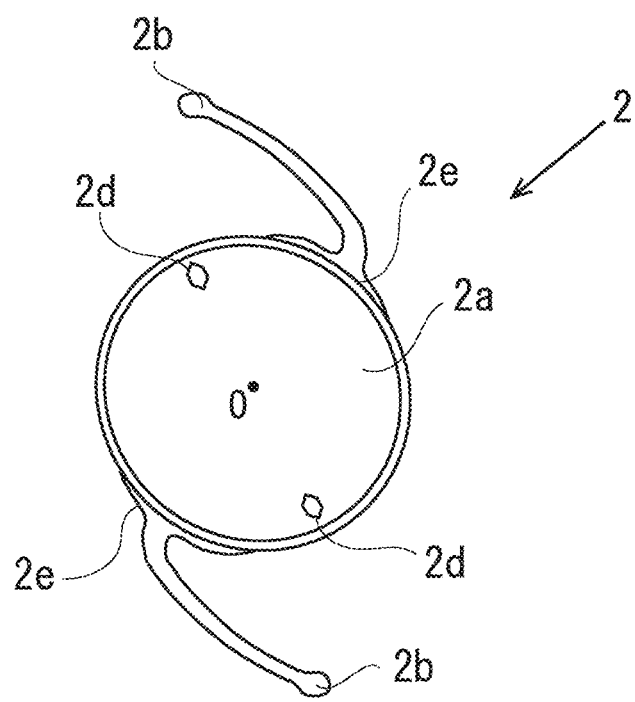
FIG. 1A is a diagram schematically illustrating a configuration of a toric intraocular lens according to one embodiment.
Figure 1B:
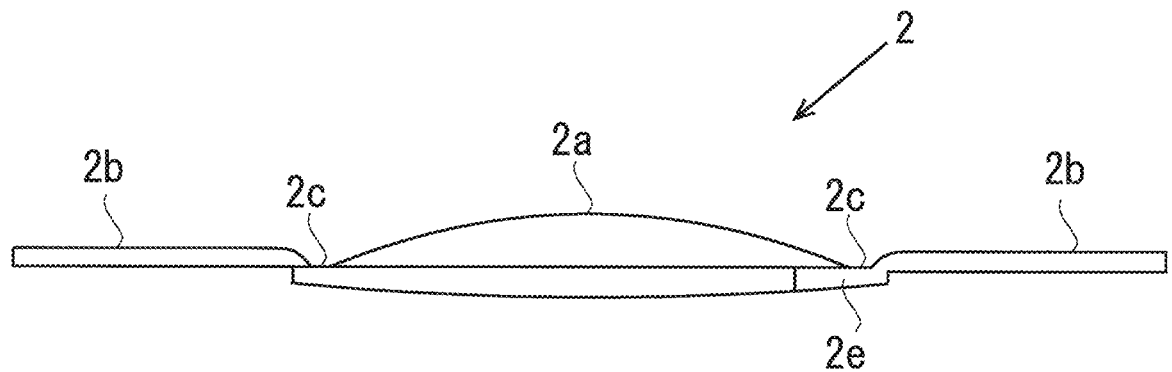
FIG. 1B is another diagram schematically illustrating a configuration of a toric intraocular lens according to one embodiment.

FIG. 1 schematically illustrates a configuration of a toric intraocular lens 2 according to the present embodiment. FIG. 1A is a plan view thereof and FIG. 1B is a side view thereof. The orientations regarding the toric intraocular lens 2 in FIGS. 1A and 1B do not correspond to each other. The toric intraocular lens 2 is what is called one-piece type toric intraocular lens, in which the lens portion and the support portion are made of the same material and integrally molded, and the material of the lens is soft acrylic material. The toric intraocular lens 2 includes a lens body 2a having a predetermined refractive power and two elongated planate support portions 2b that are connected to the lens body 2a and are provided for holding the lens body 2a inside of the eyeball. The lens body 2a and the support portions 2b are made of flexible resin material. In addition, the lens body 2a and the support portions 2b are connected with each other via the connecting portion 2e.

As illustrated in FIG. 1B, the connecting portion 2e is formed to protrude in the shape of a tangent from the circumference of the lens and to contact the circumference of the lens body 2a in a predetermined range. Further, in the present embodiment, a pair of marks 2d that face each other across the optical axis O of the lens body 2a are provided in the vicinity of the peripheral edge of the lens body 2a. A virtual line connecting the marks 2d represents the flat meridian of the lens body 2a, and a virtual line that is orthogonal to the virtual line connecting the marks 2d at the optical axis O represents the steep meridian of the lens body 2a. Therefore, after an operator inserts the toric intraocular lens 2 into the eyeball of the patient, the operator can adjust the position of the toric intraocular lens 2 such that the steep meridian direction of the cornea of the patient matches with the flat meridian direction represented by the mark 2d of the lens body 2a.

In the intraocular lens insertion apparatus 1 as described below according to the present embodiment, the toric intraocular lens 2 is set on the stage member such that one of the two support portions 2b is disposed posterior to the lens body 2a and the other of the two support portions 2b is disposed anterior to the lens body 2a. It is noted that the support portion disposed anterior to the lens body 2a is referred to as the anterior support portion and the support portion disposed posterior to the lens body 2a is referred to as the posterior support portion.

A surface roughening is applied to the support portions 2b of the toric intraocular lens 2 according to the present embodiment. Therefore, the posture of the toric intraocular lens 2 can be stabilized when the toric intraocular lens 2 is pushed and moved by the plunger 30. Specifically, when the toric intraocular lens 2 is pushed and moved by the plunger 30, preferable friction force occurs between the support portions 2b and the inner wall surface of the nozzle body 10 to prevent the toric intraocular lens 2 from rotating in the nozzle body 10. In addition, since the surface roughening is applied to the support portions 2b, the support portions 2b are prevented from sticking to the lens body 2a when the toric intraocular lens 2 is folded in the nozzle body 10. Further, in the present embodiment, since an optical surface 2c with a relatively small curvature for smoothing the gradient of the optical surface of the lens body 2a is provided for a peripheral portion of the lens body 2a, that is, a portion for connecting the lens body 2a with the support portion 2b as illustrated in FIG. 1B, the thickness of the lens at the center thereof and the cross section area of the lens are decreased to achieve a thin lens profile. The optical surface 2c may be configured to be a flat profile.

Since the diameter of the optical portion on the anterior surface in the area in which the connecting portion 2e contacts the circumference of the lens body 2a is configured to be slightly larger than the diameters in other areas due to processing margin, the shape of the optical portion on the anterior surface is slightly oval (non circular). In addition, as for the optical portion on the posterior surface, the diameter thereof in the area in which the connecting portion 2e contacts the circumference of the lens body 2a is configured to be 10% larger than the diameters in other areas. That is, the connecting portion 2e also has a portion that functions as an optical lens surface. With such configuration, the effective lens area can be as large as possible in a predetermined dimension defined for the lens body 2a. Generally, the diameter of the optical portion of the lens body 2a in the area in which the lens body 2a does not contact the connecting portion 2e ranges from 5.5 mm to 7.0 mm.

FIG. 2 schematically illustrates a configuration of the intraocular lens insertion apparatus 1 used for inserting the toric intraocular lens into the eyeball according to the present embodiment. FIG. 2A illustrates a plan view of the intraocular lens insertion apparatus 1 in a state where a stage lid member 13 is opened. FIG. 2B illustrates a side view of the intraocular lens insertion apparatus 1 in a state where the stage lid member 13 is closed. A nozzle body 10 of the intraocular lens insertion apparatus 1 is a tube member with an approximately rectangular cross section. The nozzle body 10 includes a rear end portion 10b with a wide opening formed at one end of the nozzle body 10. The nozzle body 10 includes a nozzle portion 15 and a distal end portion 10a that are configured as a narrowed insertion tube 100 at the other end of the nozzle body 10. As illustrated in FIG. 2B, the opening of the distal end portion 10a is formed into a bevel. The plunger 30 is inserted into the nozzle body 10 and can be moved to-and-fro in the nozzle body 10.

In the descriptions hereinafter, the direction extending toward the distal end portion 10a from the rear end portion 10b of the nozzle body 10 is assumed as the frontward direction, the direction opposite to the frontward direction is assumed as the rearward direction, the direction toward a viewer's side with respect to a paper surface on which FIG. 2A is drawn is assumed as the upward direction, the direction opposite to the upward direction is assumed as the downward direction, the direction toward a viewer's side with respect to a paper surface on which FIG. 2B is drawn is assumed as the leftward direction, and the direction opposite to the leftward direction is assumed as the rightward direction. In this case, the upward direction corresponds to a direction toward a front side along an optical axis of a lens body 2a described later, the downward direction corresponds to a direction toward a rear side along the optical axis of the lens body 2a, the frontward direction corresponds to a direction toward a front side in the push direction of the plunger 30, and the rearward direction corresponds to a direction toward a rear side in the push direction of the plunger 30.

A hold member 11 which projects in a plate shape and on which a user hooks the user's fingers when the user pushes the plunger 30 toward the distal end side of the nozzle body 10 is integrally formed on the nozzle body 10 in the vicinity of the rear end portion 10b of the nozzle body 10. In addition, the stage member 12 on which the toric intraocular lens 2 is to be set is formed on the rear end side of the nozzle portion 15 of the nozzle body 10. The stage member 12 is configured to be opened toward an upper side of the nozzle body 10 by opening the stage lid member 13. Further, the positioning member 50 is mounted on the stage member 12 from below the nozzle body 10. With the use of the positioning member 50, the toric intraocular lens 2 is stably positioned and held on the stage member 12 even before the insertion apparatus is used (during transportation).

That is, in the intraocular lens insertion apparatus 1, at the time of manufacturing the intraocular lens insertion apparatus 1, the toric intraocular lens 2 is set on the stage member 12 such that a front side along an optical axis is directed upward in a state where the stage lid member 13 is opened and the positioning member 50 is mounted on the stage member 12. Then, the intraocular lens insertion apparatus 1 is commercially distributed with the stage lid member 13 closed, and the intraocular lens insertion apparatus 1 is sold. When the user uses the intraocular lens insertion apparatus 1, the user insert a needle of an injector which lubricant for the toric intraocular lens is filled with into the stage member 12 through a needle hole 20a of the insertion portion 20 and the lubricant is injected therein. Then, the user removes the positioning member 50 while holding the stage lid member 13 in a closed state and, thereafter, pushes the plunger 30 toward the distal end side of the nozzle body 10.

Due to such an operation, the toric intraocular lens 2 is pushed to the nozzle portion 15 by the plunger 30, and the toric intraocular lens 2 is ejected into the inside of the eyeball from the distal end portion 10a. In the intraocular lens insertion apparatus 1, the nozzle body 10, the plunger 30, and the positioning member 50 are formed using a resin such as polypropylene. Polypropylene has been proven as a material used for medical apparatuses. In addition, polypropylene is reliable in chemical resistance etc.

In addition, a check window 17 is provided on a part of the stage lid member 13 by forming the part to be thinner than the other parts. The extent how thin the check window 17 is formed on the stage lid member 13 can be appropriately determined based on the material used for the stage lid member 13 and the visibility of the toric intraocular lens checked from the check window 17. Further, since the check window 17 is formed, it is expected that a sink that occurs when the stage lid member 13 is formed can be effectively reduced.

Figure 3:
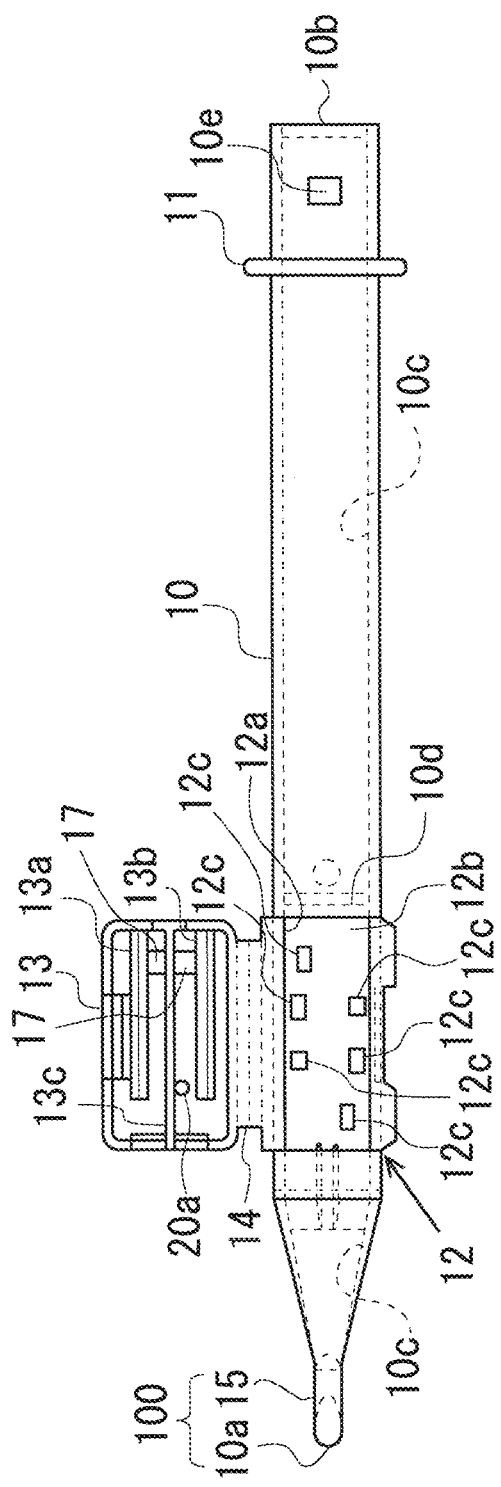
FIG. 3 is a diagram schematically illustrating a configuration of a nozzle body according to one embodiment.

FIG. 3 is a plan diagram of the nozzle body 10. As described previously, in the nozzle body 10, the toric intraocular lens 2 is set on the stage member 12. In such a state, the toric intraocular lens 2 is pushed by the plunger 30, and is released from the distal end portion 10a. Here, a through-hole 10c whose cross-sectional shape changes corresponding to a change in a profile of the nozzle body 10 is formed in the inside of the nozzle body 10. In the release of the toric intraocular lens 2, the toric intraocular lens 2 is deformed corresponding to a change in a cross-sectional shape of the through-hole 10c formed in the inside of the nozzle body 10, and is released after being deformed into a shape which facilitates the entrance of the toric intraocular lens 2 into the incision formed in the eyeball of the patient.

Further, the distal end portion 10a has an obliquely cut shape, what is called bevel cut shape, such that an upper region of the nozzle portion 15 extends more toward a front side than a lower region of the nozzle portion 15. The details of the distal end of the nozzle portion 15 according to the present embodiment are described later. The obliquely cut shape of the distal end portion 10a may be formed by obliquely cutting the distal end portion 10a so as to have a straight line shape as viewed from a rightward and leftward direction or may be formed by obliquely cutting the distal end portion 10a so as to have an outwardly bulging shape or a curved surface shape.

A stage groove 12a having a width slightly larger than a diameter of the lens body 2a of the toric intraocular lens 2 is formed on the stage member 12. A size of the stage groove 12a in a frontward and rearward direction is set to be larger than a total size of the toric intraocular lens 2 including the support portions 2b extending to both sides of the toric intraocular lens 2. In addition, a setting surface 12b as a surface on which the toric intraocular lens is placed is formed of a bottom surface of the stage groove 12a. The position of the setting surface 12b in an upward and downward direction is set higher than the height position of a bottom surface of the through-hole 10c formed in the nozzle body 10, and the setting surface 12b and the bottom surface of the through-hole 10c are connected to each other by a bottom inclined surface 10d.

The stage member 12 and the stage lid member 13 are integrally formed with each other. A size of the stage lid member 13 in the frontward and rearward direction is set to be substantially equal to a size of the stage member 12 in the frontward and rearward direction. The stage lid member 13 is connected to the stage member 12 by a thin-plate-like connection member 14 which is formed in an extending manner toward the stage lid member 13 side from a side surface of the stage member 12. The connection member 14 is formed in a bendable manner at a center portion thereof, and the stage lid member 13 overlaps with the stage member 12 from above by bending the connection member 14 so that the stage lid member 13 is closed.

In the stage lid member 13, ribs 13a, 13b for reinforcing the stage lid member 13 and for stabilizing the position of the toric intraocular lens 2 are formed on a surface of the stage lid member 13 which faces the setting surface 12b in an opposed manner in a lid closed state. A guide projection 13c is formed on the stage lid member 13 as an upper guide for the plunger 30. Further, the needle hole 20a is formed in the stage lid member 13 as an insertion hole for injecting a hyaluronic acid into the stage member 12 using an injector before an operation of inserting the toric intraocular lens 2 into the eyeball is performed. The needle hole 20a is a hole which connects the outside of the stage member 12 and the toric intraocular lens 2 housed in the stage member 12 to each other when the stage lid member 13 is closed. A user inserts a needle of an injector through the needle hole 20a before the insertion operation of the toric intraocular lens 2 is performed, and supplies hyaluronic acid that is a viscoelastic material to the necessary position in the inside of the stage member 12.

Figure 4A:
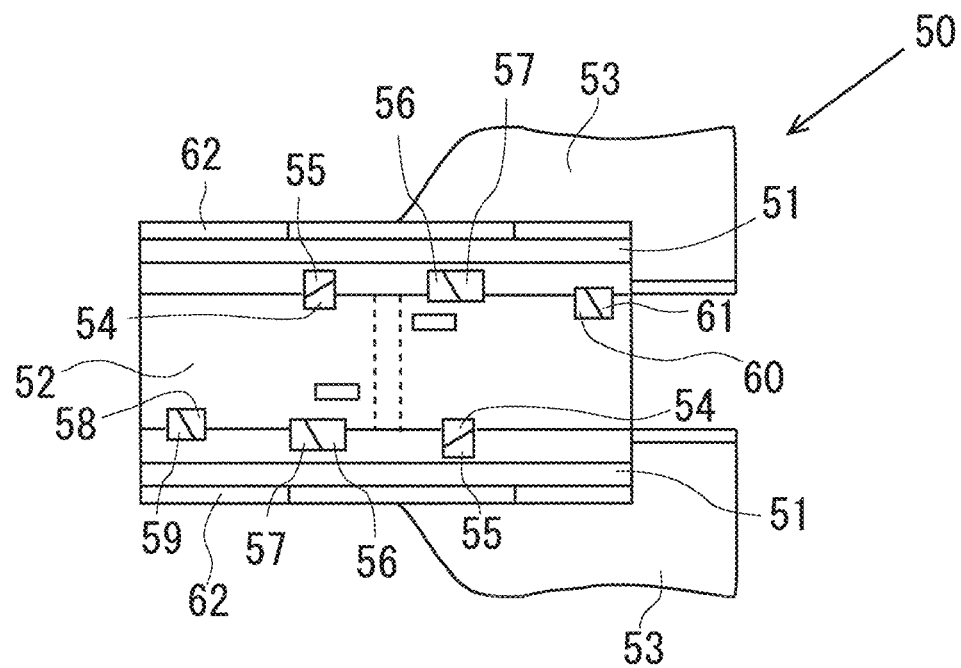
FIG. 4A is a diagram schematically illustrating a configuration of a positioning member according to one embodiment.
Figure 4B:
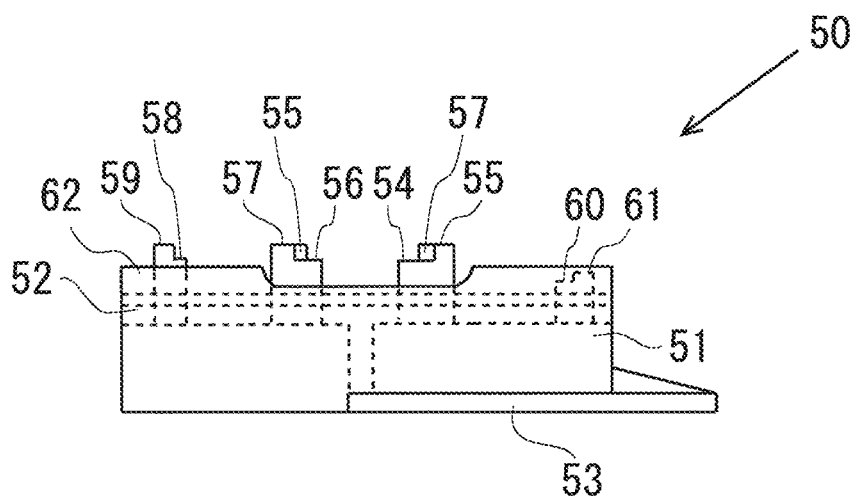
FIG. 4B is another diagram schematically illustrating a configuration of a positioning member according to one embodiment.

The positioning member 50 is detachably mounted on a lower side of the setting surface 12b of the stage member 12. FIG. 4 illustrates a schematic configuration of the positioning member 50. FIG. 4A is a plan diagram of the positioning member 50, and FIG. 4B is a left side diagram of the positioning member 50. The positioning member 50 is formed as a body separate from the nozzle body 10, and is configured such that a pair of side wall portions 51, 51 is connected to each other by a connecting portion 52. Holding portions 53, 53 which extend and expand outwardly are formed on the lower ends of the side wall portions 51, respectively.

A pair of first placing portions 54, 54 which projects upward is formed inside of the respective side wall portions 51, 51. In addition, first positioning portions 55, 55 are formed on the outer peripheral sides of the upper end surfaces of the first placing portions 54, 54 in a projecting manner. A distance between the inside surfaces of the first positioning portions 55, 55 is set to be slightly larger than a diameter size of the lens body 2a of the toric intraocular lens 2.

Further, a pair of second placing portions 56, which projects upward is formed inside of the respective side wall portions 51, 51. A height of the upper surfaces of the second placing portions 56, 56 is set to be substantially equal to a height of the upper surfaces of the first placing portions 54, 54. In addition, second positioning portions 57, 57 which project further upward are formed on the outer portions of the upper surfaces of the second placing portions 56, 56 such that the second positioning portions 57, 57 extend over the whole regions of the second placing portions 56, 56 in the rightward and leftward direction. A distance between the inside surfaces of the second positioning portions 57, 57 is set to be slightly larger than the diameter size of the lens body 2a of the toric intraocular lens 2.

In addition, the third placing portion 58 on which a part of the anterior support portion of the support portions 2b of the toric intraocular lens 2 is formed inside of the respective side wall portions 51, 51. Further, the third positioning portion 59 which projects further upward from the third placing portion 58 is formed. A part of the anterior support portion contacts the third positioning portion 59. Moreover, the fourth placing portion 60 on which a part of the posterior support portion of the support portions 2b of the toric intraocular lens 2 is formed inside of the respective side wall portions 51, 51. In addition, the fourth positioning portion 61 which projects further upward from the fourth placing portion 60 is formed. A part of the posterior support portion contacts the fourth positioning portion 61. As illustrated in FIG. 4B, heights of the upper surfaces of the fourth placing portion 60 and the fourth positioning portion 61 are set to be substantially lower than the heights of the upper surfaces of the first, second, and third placing portions and the first, second, and third positioning portions. On the other hand, anti-rotation wall portions 62 for preventing an unnecessary rotation of the positioning member 50 when the positioning member is detached are provided on the outer side of the respective side wall portions 51, 51.

The above-mentioned positioning member 50 is assembled to the nozzle body 10 from below the setting surface 12b of the nozzle body 10. The setting surface through-holes 12c which penetrate the setting surface 12b in the thickness direction are formed in the setting surface 12b of the nozzle body 10. The profiles of the setting surface through-holes 12c have shapes slightly larger than and substantially similar to the shapes of the first to fourth placing portions or the shapes of the first to fourth positioning members of the positioning member 50 as viewed from above. When the positioning member 50 is mounted on the nozzle body 10, the first to fourth placing portions and the first to fourth positioning portions are inserted into the setting surface through-holes 12c from below the setting surface 12b, and project upward from the setting surface 12b.

Then, in setting the toric intraocular lens 2 on the setting surface 12b, a bottom surface of an outer peripheral portion of the lens body 2a is placed on the upper surfaces of the first placing portions 54, 54 and the upper surfaces of the second placing portions 56, 56. The position of the lens body 2a in a horizontal direction (a direction horizontal to the setting surface 12b) is restricted by the first positioning portions 55, 55 and the second positioning portions 57, 57. Further, each of the two support portions 2b of the toric intraocular lens 2 is placed on the upper surface of the third placing portion 58 and the upper surface of the fourth placing portion 60. Additionally, the position of each of the two support portions 2b in the horizontal direction is restricted by the third positioning portion 59 and the fourth positioning portion 61.

FIG. 5 illustrates the schematic configuration of the plunger 30. A length of the plunger 30 in the frontward and rearward direction is set slightly larger than that of the nozzle body 10. The plunger 30 is formed of an operating member 31 which is disposed on a distal end side and basically has a circular columnar shape, and an insertion member 32 which is disposed on a rear end side and basically has a rectangular rod shape. The operating member 31 is configured to include a circular columnar portion 31a having a circular columnar shape, and a thin-plate-shaped flat portions 31b expanding in the rightward and leftward direction from the circular columnar portion 31a. FIG. 5A illustrates the central axis CX of the operating member 31 (the circular columnar portion 31a) of the plunger 30. The width (thickness) of the distal end portion of the plunger 30 is generally from 0.5 mm to 2.0 mm. Since the strength of the plunger becomes lower when the width becomes smaller than this general width, the lens may not be pushed in a stable manner. On the other hand, the size of the incision for inserting the intraocular lens becomes larger when the width becomes larger than this general width, astigmatism what is called induced astigmatism may occur to adversely influence on the patient's visual performance.

A notch 31c is formed on a distal end portion of the operating member 31. As can be understood from FIG. 5B, the notch 31c is formed in a groove-like shape on the operating member 31 to open downward and penetrate the operating member 31 in the rightward and leftward direction. As can be understood from FIG. 5B, a groove wall disposed on a distal end side of the notch 31c is formed of an inclined surface which extends downward as the inclined surface extends toward the distal end side of the operating member 31.

In addition, slits 31d, 31f are respectively formed in the middle of the right and left flat portions 31b in the frontward and rearward direction and near the rear end of the right and left flat portions 31b. The slits 31d, 31f are formed in an approximately L-shape by a combination of a cut extending in the rightward and leftward direction of the flat portion 31b and a cut extending in the frontward and rearward direction of the flat portion 31b. In addition, movable segments 31e, 31g are formed on the flat portion 31b by forming the slits 31d, 31f. The movable segments 31e, 31g function as what is called axis-shift prevention such that the circular columnar member 31a is positioned at the center in the rightward and leftward direction of the nozzle body 10 when the plunger 30 moves in the nozzle body 10. Although two pairs of the movable segments 31e, 31g are formed in the present embodiment, only one pair of the movable segments or more than two pairs of the movable segments can be formed instead.

The insertion member 32 has an approximately H-shaped cross section as a whole, and a size of the insertion member 32 in the rightward and leftward direction and a size of the insertion member 32 in the upward and downward direction are set slightly smaller than those of the through-hole 10c formed in the nozzle body 10. A disc-shaped pushing plate member 33 which expands in the upward and downward direction as well as in the rightward and leftward direction is formed on a rear end of the insertion member 32.

A pawl portion 32a which projects toward an upper side of the insertion member 32 and is movable in the upward and downward direction due to elasticity of a raw material of the plunger 30 is formed on a portion of the insertion member 32 on a distal end side from the center in the frontward and rearward direction. When the plunger 30 is inserted into the nozzle body 10, an engaging hole 10e illustrated in FIG. 3 which is formed in the upper surface of the nozzle body 10 in a thickness direction and the pawl portion 32a are engaged with each other. With such engagement, the relative position between the nozzle body 10 and the plunger 30 in an initial state is determined. The position where the pawl portion 32a is formed and the position where the engaging hole 10e is formed are set such that, in an engaging state, a distal end of the operating member 31 is positioned behind the lens body 2a of the toric intraocular lens 2 set on the stage member 12, and the support portion 2b on a rear side of the lens body 2a can be held by the notch 31c from above. Further, similar to the slits 31d, 31f, an approximately L-shaped slit formed by a cut extending in the rightward and leftward direction and a cut extending in the frontward and rearward direction can be formed on the insertion member 32. Such a slit formed on the insertion member also functions as axis-shift prevention of the plunger 30.

FIGS. 6A, 6B, 6C, 6D, 7A, 7B, 7C, and 7D schematically illustrate prototype toric intraocular lenses 110, 120, 130, 140, 150, 160, 170, and 180 in the present embodiment, respectively. In each of FIGS. 6A, 6B, 6C, 6D, 7A, 7B, 7C, and 7D, the axis corresponding to the central axis CX of the plunger 30 when the toric intraocular lenses 110, 120, 130, 140, 150, 160, 170, and 180 are set on the stage member 12 is the axis AX. Thus, the toric intraocular lenses 110, 120, 130, 140, 150, 160, 170, and 180 are pushed in the direction of the axis AX by the plunger 30 in the intraocular lens insertion apparatus 1. In addition, the axis that is orthogonal to the axis AX on the plane that is perpendicular to the directions of the optical axes of the toric intraocular lenses 110, 120, 130, 140, 150, 160, 170, and 180 (the plane that is parallel to the plane of the paper) is the axis BX. Further, the axis that passes through the center of the optical axis of the lens body and connects the pair of connecting portions with each other is the axis DX. And the position on the circumference of the lens body at which the tip of the plunger 30 contacts the lens body is the position P. Moreover, the angle between the flat meridian of the lens body and the axis (the axis AX) in the push direction of the plunger 30 is θ.

In the present embodiment, as illustrated in FIGS. 6A, 6B, 6C, 6D, 7A, 7B, 7C, and 7D, marks 110d, 120d, 130d, 140d, 150d, 160d, 170d, and 180d for indicating the directions of the flat meridian are provided for the lens bodies 110a, 120a, 130a, 140a, 150a, 160a, 170a, and 180a of the toric intraocular lenses 110, 120, 130, 140, 150, 160, 170, and 180 as is the case with the mark 2d of the toric intraocular lens 2. The marks 110d, 120d, 130d, 140d, 150d, 160d, 170d, and 180d are provided as a pair of marks near both ends of the flat meridian of the lens bodies 110a, 120a, 130a, 140a, 150a, 160a, 170a, and 180a, respectively.

The thickness of each of the lens bodies 110a, 120a, 130a, 140a, 150a, 160a, 170a, and 180a on the plane that is perpendicular to each of the optical axes of the lens bodies 110a, 120a, 130a, 140a, 150a, 160a, 170a, and 180a becomes largest in the direction of the flat meridian. The thickness of the lens body here means the thickness of the lens body on the circumference (edge thickness). And the thicknesses of each of the lens bodies 110a, 120a, 130a, 140a, 150a, 160a, 170a, and 180a in other directions that pass through the center of the lens body become smaller than the thickness of the lens body in the direction of the flat meridian. More specifically, it is assumed for each of the lens bodies 110a, 120a, 130a, 140a, 150a, 160a, 170a, and 180a that there is a line that overlaps the flat meridian and passes through the center of the lens body on the plane that is perpendicular to the optical axis. Further, it is assumed that the line is rotated clockwise or counterclockwise to overlap the virtual line DX connecting the connecting portions of the respective pair of connecting portions 110e, 120e, 130e, 140e, 150e, 160e, 170e, and 180e of the lens bodies 110a, 120a, 130a, 140a, 150a, 160a, 170a, and 180a. In this case, as the rotation angle from the direction of the flat meridian becomes larger, the thickness of the each of the lens bodies 110a, 120a, 130a, 140a, 150a, 160a, 170a, and 180a in the direction of the rotated line becomes smaller to reach a minimal value. Then, the thickness becomes larger as the direction that passes the center of the respective lens bodies 110a, 120a, 130a, 140a, 150a, 160a, 170a, and 180a becomes closer to the direction represented by the virtual line DX connecting the connecting portions of the respective pair of connecting portions 110e, 120e, 130e, 140e, 150e, 160e, 170e, and 180e of the lens bodies 110a, 120a, 130a, 140a, 150a, 160a, 170a, and 180a.

In the present embodiment, the virtual line DX connecting the connecting portions of the respective pair of connecting portions 110e, 120e, 130e, 140e, 150e, 160e, 170e, and 180e is defined as a line indicating that the thickness of the lens body 2a reaches a maximal value in that direction. The virtual line DX is not limited to one of the lines illustrated in FIGS. 6A, 6B, 6C, 6D, 7A, 7B, 7C, and 7D as long as the virtual line DX passes through the center of the respective lens bodies 110a, 120a, 130a, 140a, 150a, 160a, 170a, and 180a and connects predetermined points of the respective connecting portions 110e, 120e, 130e, 140e, 150e, 160e, 170e, and 180e with each other.

Figure 6A:
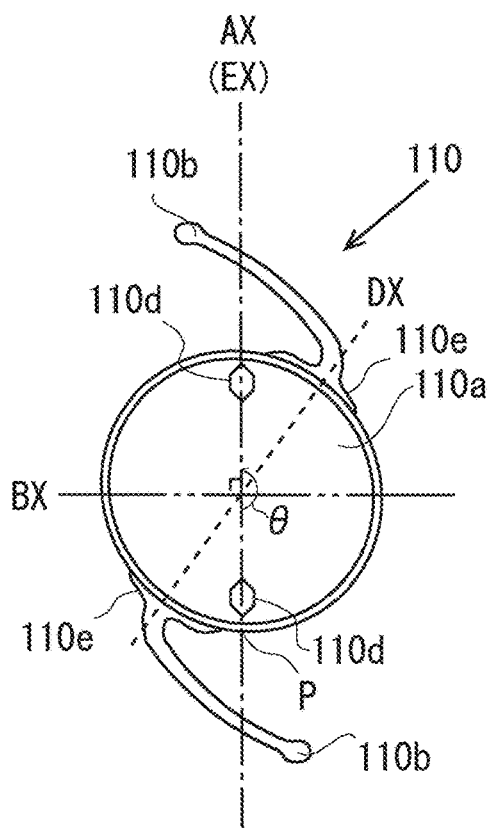
FIG. 6A is a diagram schematically illustrating a configuration of a toric intraocular lens in a case where an axis shift of a plunger occurs and in a case where the axis shift of the plunger does not occur.
Figure 6B:
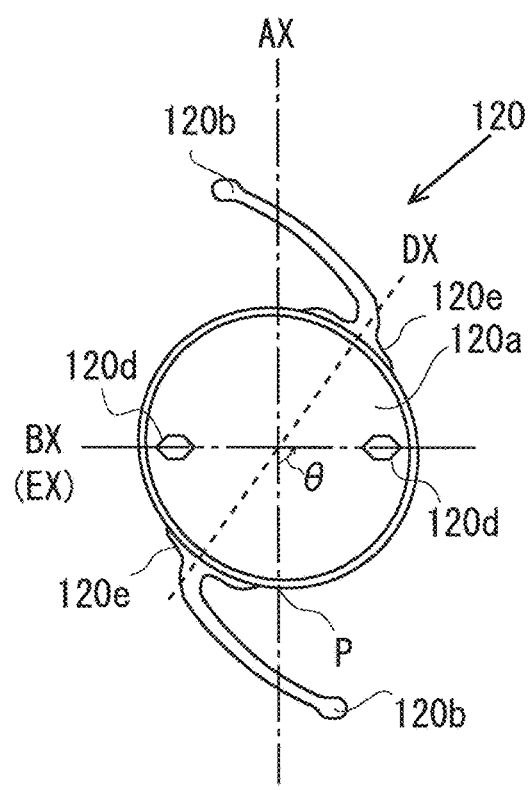
FIG. 6B is another diagram schematically illustrating a configuration of a toric intraocular lens in a case where an axis shift of a plunger occurs and in a case where the axis shift of the plunger does not occur.
Figure 6C:
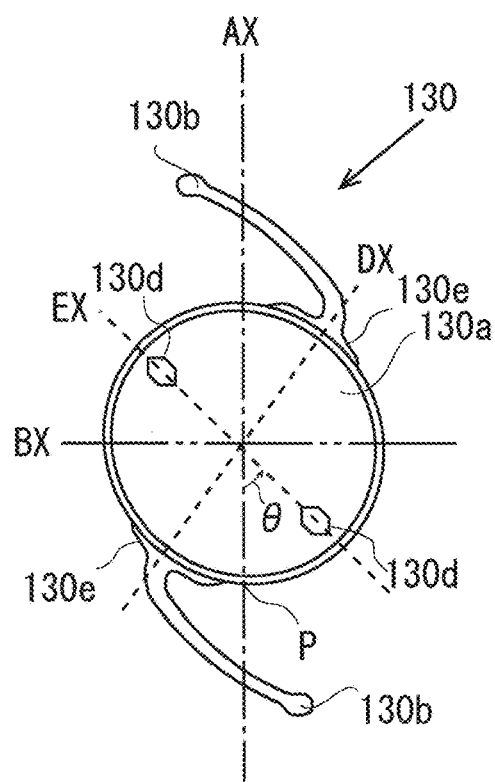
FIG. 6C is yet another diagram schematically illustrating a configuration of a toric intraocular lens in a case where an axis shift of a plunger occurs and in a case where the axis shift of the plunger does not occur.
Figure 6D:
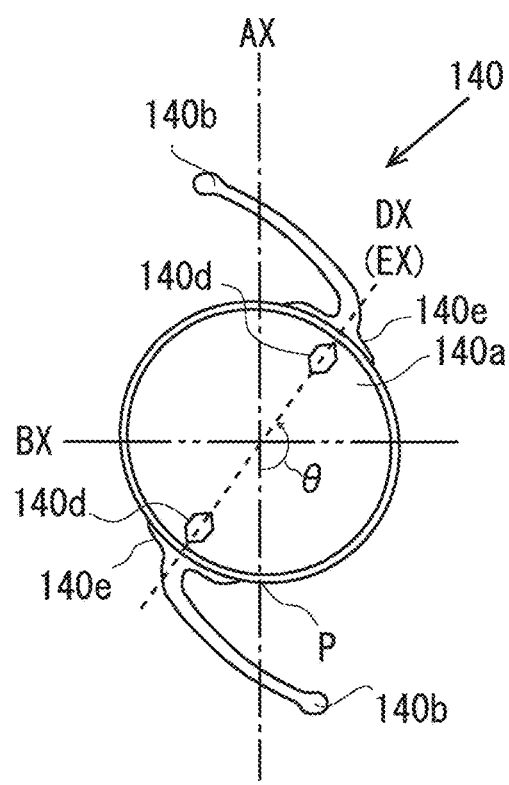
FIG. 6D is further another diagram schematically illustrating a configuration of a toric intraocular lens in a case where an axis shift of a plunger occurs and in a case where the axis shift of the plunger does not occur.

Therefore, as for the thickness of the lens body 110a of the toric intraocular lens 110 as illustrated in FIG. 6A, for example, when a line that overlaps the axis AX and passes through the center of the lens body 110a rotates clockwise, the thickness reaches a maximal value in the axis AX direction, reaches a minimal value in a direction between the axis AX and the axis DX, reaches a maximal value in the axis DX direction, reaches a minimal value in a direction between the axis DX and the axis AX, and then reaches a maximal value in the axis AX direction. That is, the thickness of the lens body 110a varies to reach maximal values and minimal values between the flat meridian and the axis DX of the lens body 110a. The thicknesses of the other lens bodies 120a, 130a, 140a, 150a, 160a, 170a, and 180a are expected to vary in a similar manner.

Figure 8A:
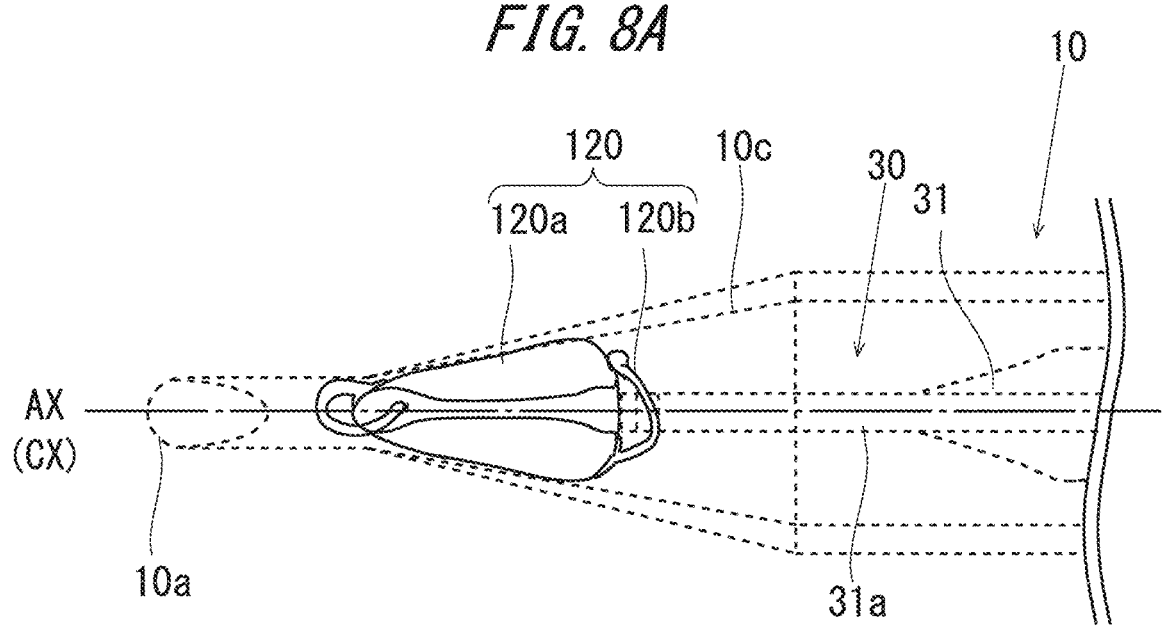
FIG. 8A is a diagram exemplifying a case where an axis shift of a plunger occurs when the plunger pushes the toric intraocular lens as illustrated in FIGS. 6A to 6D and FIGS. 7A to 7D and a case where the axis shift of the plunger does not occur.
Figure 8B:
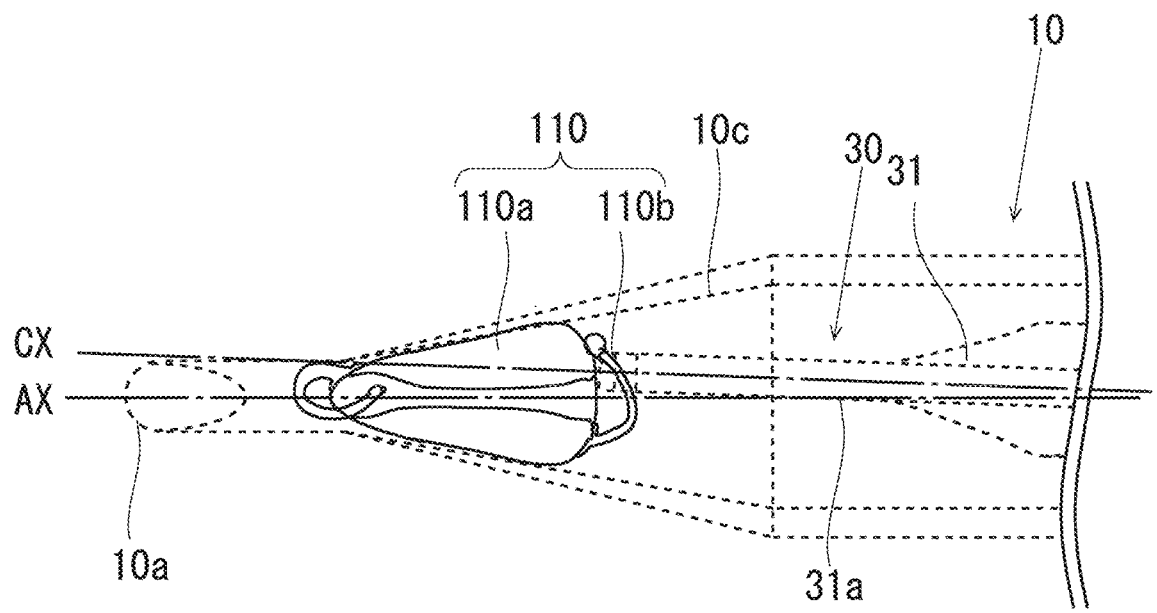
FIG. 8B is another diagram exemplifying a case where an axis shift of a plunger occurs when the plunger pushes the toric intraocular lens as illustrated in FIGS. 6A to 6D and FIGS. 7A to 7D and a case where the axis shift of the plunger does not occur.
Figure 10A:
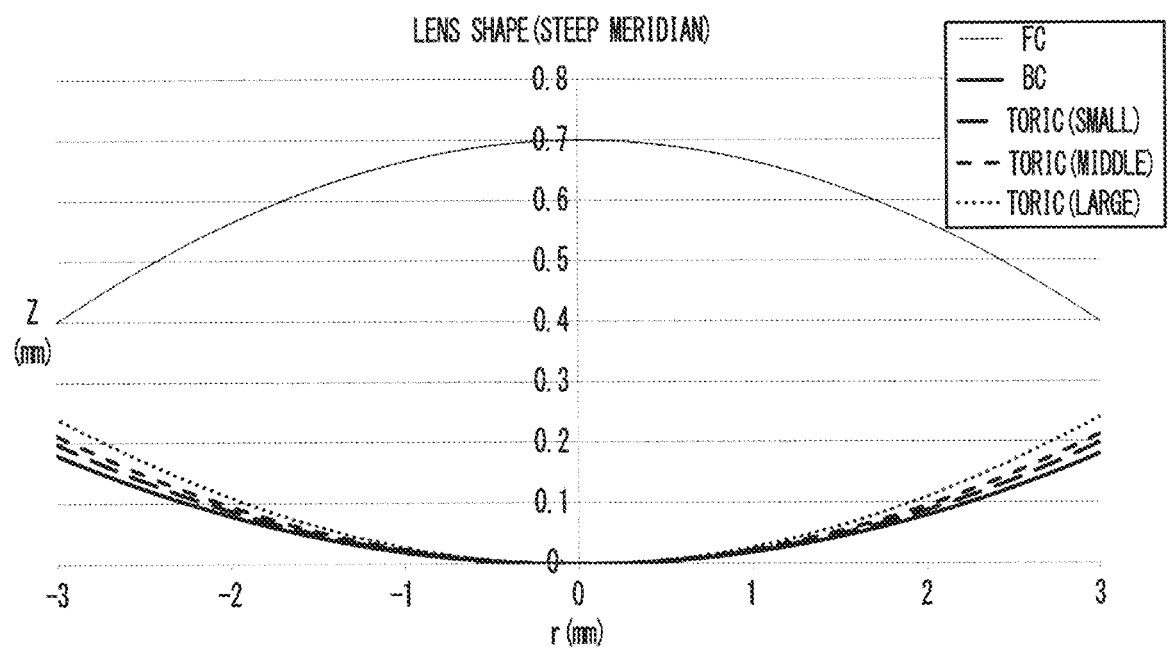
FIG. 10A is a diagram illustrating an example of a cross-sectional shape of a toric intraocular lens with respect to the optical axis thereof according to one embodiment.
Figure 10B:
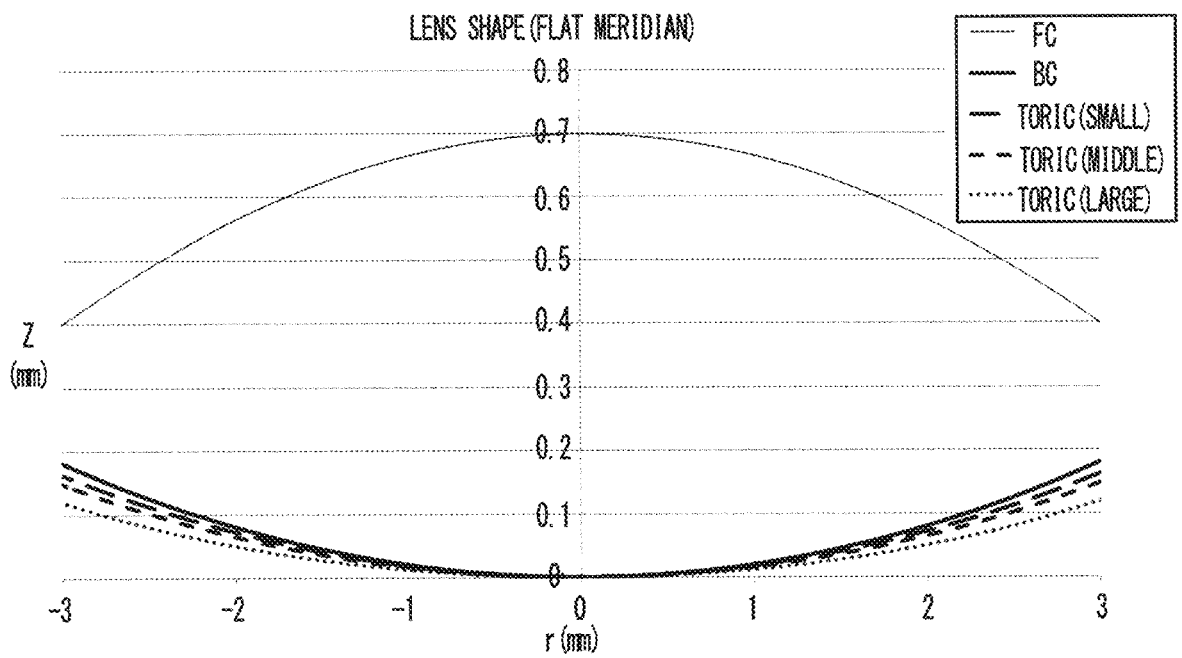
FIG. 10B is another diagram illustrating an example of a cross-sectional shape of a toric intraocular lens with respect to the optical axis thereof according to one embodiment.
Figure 11A:
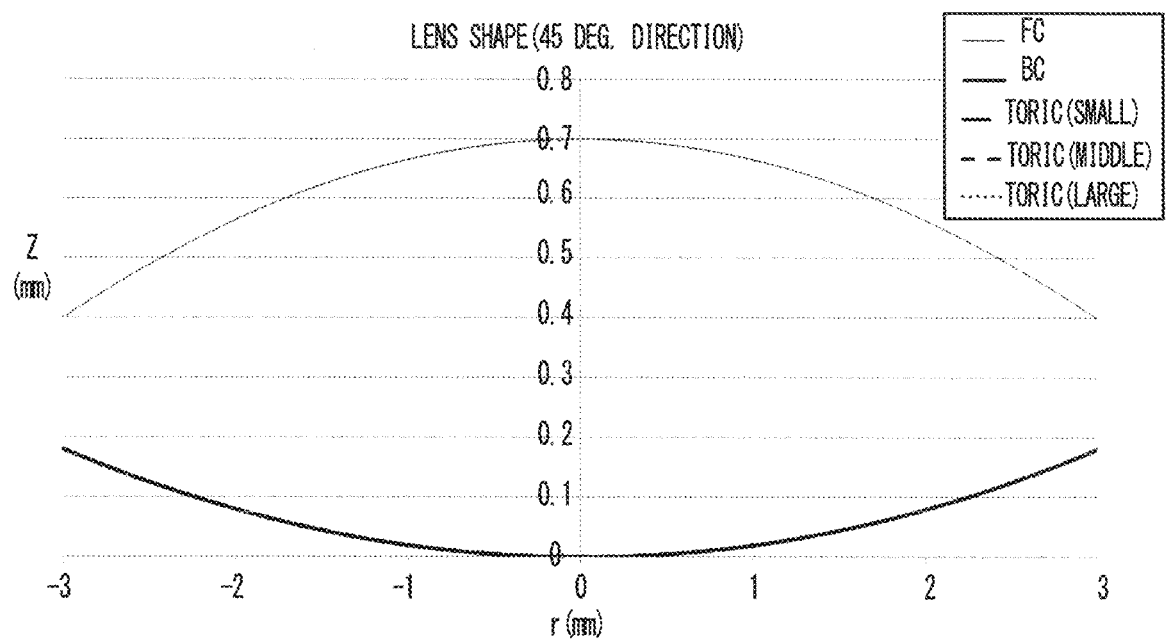
FIG. 11A is a diagram illustrating another example of a cross-sectional shape of a toric intraocular lens with respect to the optical axis thereof according to one embodiment.
Figure 11B:
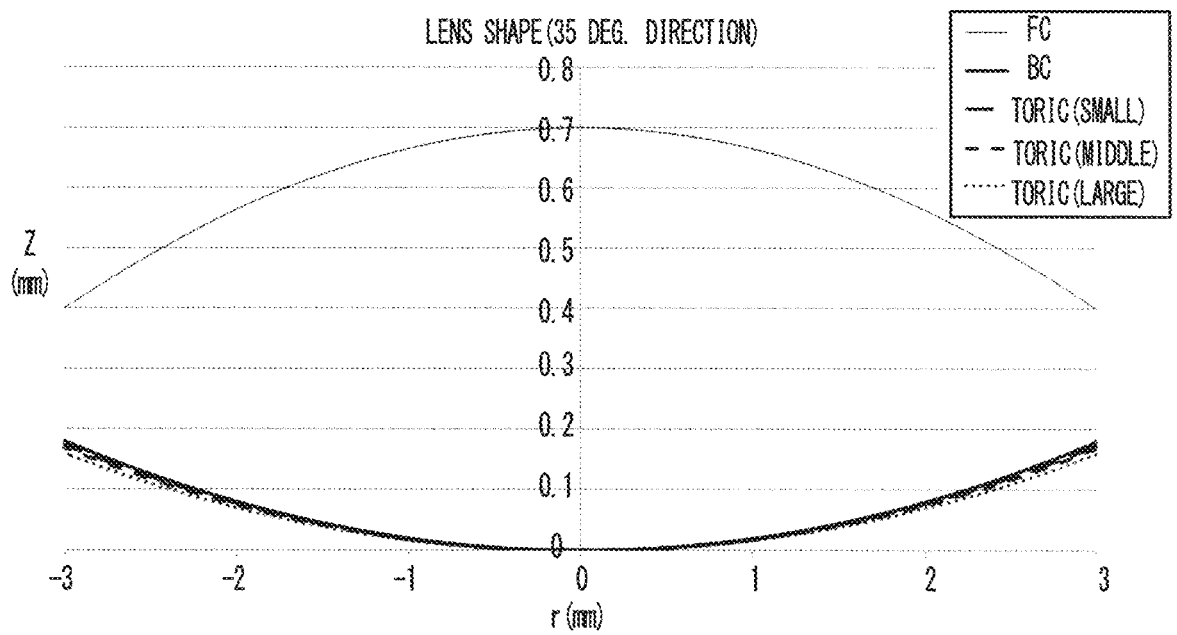
FIG. 11B is another diagram illustrating another example of a cross-sectional shape of a toric intraocular lens with respect to the optical axis thereof according to one embodiment.
Figure 12:
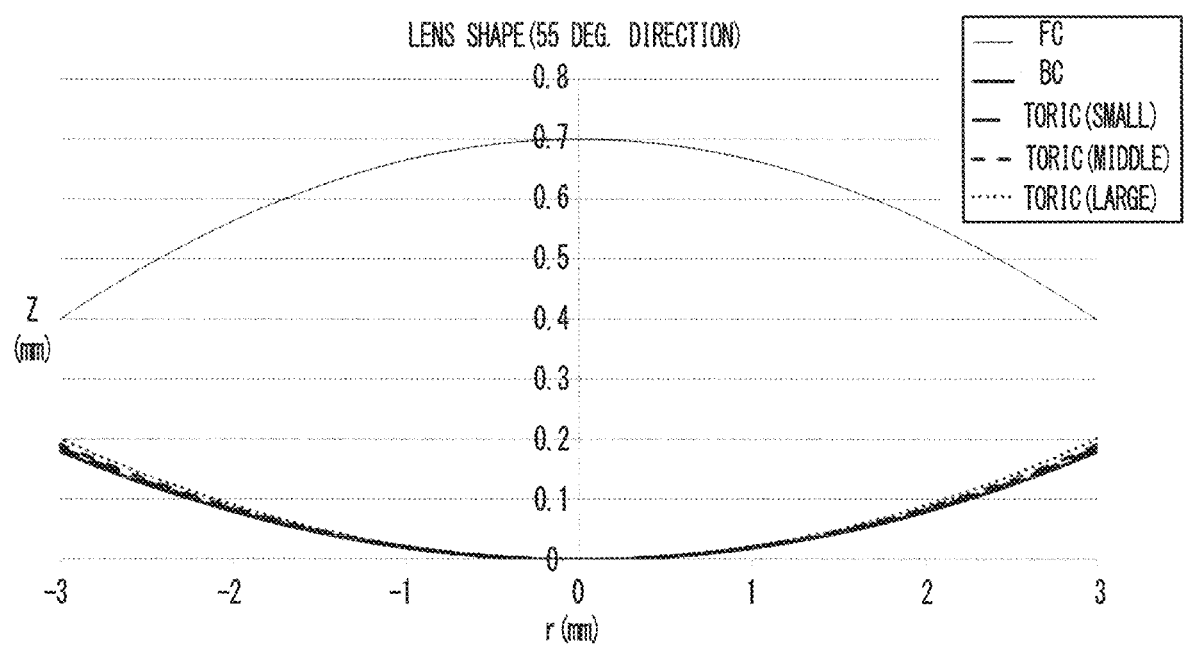
FIG. 12 is a diagram illustrating yet another example of a cross-sectional shape of a toric intraocular lens with respect to the optical axis thereof according to one embodiment.

Next, the relations between the position of the toric intraocular lenses 110, 120, 130, 140, 150, 160, 170, and 180 and the position of the plunger 30 in the nozzle body 10 when the intraocular lens insertion apparatus 1 is used to push the toric intraocular lenses 110, 120, 130, 140, 150, 160, 170, and 180 in the present embodiment are described below with reference to FIG. 8A and FIG. 8B. In FIG. 8A and FIG. 8B, the nozzle body 10 and the plunger 30 are represented by broken lines and the toric intraocular lenses 110, 120 are represented by solid lines.

FIG. 8A illustrates an example of the relation between the position of the toric intraocular lens 120 and the position of the plunger 30 in the nozzle body 10 when the intraocular lens insertion apparatus 1 is used to insert the toric intraocular lens 120 into the eyeball. As described above, the thickness of the lens body 120a of the toric intraocular lens 120 reaches a maximal value in the direction indicated by the virtual line connecting the marks in the pair of marks 120d, which is identical to the axis BX in FIG. 6B, and in the direction indicated by the axis DX. That is, the position P at which the tip of the plunger 30 contacts the lens body 120a in the nozzle body 10 corresponds to a position between the two positions at which the thickness of the lens body 120a reaches the maximal value.

As a result, since the thickness of the lens body 120a on both sides of the tip of the plunger 30 is larger than the thickness of the portion at which the tip of the plunger 30 contacts the lens body 120a to prevent a shift of the position of the tip of the plunger 30 when the plunger 30 pushes the toric intraocular lens 120, the state in which the central axis CX of the plunger 30 and the push direction of the plunger 30 (the axis AX direction) match with each other can be preferably maintained.

In addition, FIG. 8B illustrates an example of the relation between the position of the toric intraocular lens 110 and the position of the plunger 30 in the nozzle body 10 when the intraocular lens insertion apparatus 1 is used to insert the toric intraocular lens 110 into the eyeball. As described above, the thickness of the lens body 110a of the toric intraocular lens 110 reaches a maximal value in the direction indicated by the virtual line connecting the marks in the pair of marks 110d, which is identical to the axis AX in FIG. 6A, and in the direction indicated by the axis DX. That is, the position P at which the tip of the plunger 30 contacts the lens body 110a in the nozzle body 10 corresponds to the portion at which the thickness of the lens body 110a reaches the maximal value.

As a result, since the thickness of the lens body 110a on both sides of the tip of the plunger 30 is smaller than the thickness of the portion at which the tip of the plunger 30 contacts the lens body 110a when the plunger 30 pushes the toric intraocular lens 110, the possibility of a shift of the position of the tip of the plunger 30 from the position at which the thickness of the lens body 110a reaches the maximal value to either side of the position increases. In this case, since the tip of the plunger 30 shifts as illustrated in FIG. 8B, the central axis CX of the plunger 30 does not match with the push direction of the plunger 30 (the axis AX direction). When the tip of the plunger 30 shifts as described above, the operations of using the plunger 30 to push the toric intraocular lens 110 cannot be performed stably and the operator's operations may be interfered.

FIG. 9 illustrates results of verification tests to check whether the tip of the plunger 30 shifts as described above when the plunger 30 is used to push the intraocular lens 110, 120, 130, 140, 150, 160, 170, and 180 with the patterns of the flat meridian as illustrated in FIGS. 6A, 6B, 6C, 6D, 7A, 7B, 7C, and 7D. Each number in the "LENS" column represents the sign attached to each toric intraocular lens as described above. In addition, the word "NONE" in the "AXIS SHIFT" column means that the toric intraocular lens can be pushed by the plunger 30 with the central axis CX of the plunger 30 and the push direction (the axis AX direction) matched as illustrated in FIG. 8A. The word "OCCUR" in the "AXIS SHIFT" column means that the central axis CX of the plunger 30 and the push direction (the axis AX direction) do not match with each other as illustrated in FIG. 8B when the toric intraocular lens is pushed by the plunger 30.

As illustrated in FIG. 9, a shift of the axis of the plunger 30 does not occur in case of the toric intraocular lenses 120, 130, 160, and 180. That is, when the toric intraocular lenses 120, 130, 160, and 180 are pushed by the plunger 30, the relation between the position of the toric intraocular lenses 120, 130, 160, and 180 and the position of the plunger 30 in the nozzle body 10 is that the central axis CX of the plunger 30 and the axis AX match with each other as illustrated in FIG. 8A. Referring to FIGS. 6B, 6C, 7B, and 7D, when one of the pair of marks indicating the flat meridian ("EX" in the drawings) of the lens body of the toric intraocular lens, that is one end of the flat meridian is located on the opposite side of the axis (axis DX) that passes through the optical center of the lens body and connects the pair of connecting portions with each other, with respect to the position ("P" in the drawings) at which the tip of the plunger 30 contacts the circumference of the lens body, and when the angle ("θ" in the drawings) between the flat meridian of the lens body and the axis (axis AX) representing the push direction of the plunger 30 is larger than 0° and equal to or smaller than 90°, it can be said that a shift of the axis of the plunger 30 does not occur. In addition, when the thickness of the lens body on its circumference is configured to reach a minimal value at the position where the tip of the plunger 30 contacts the circumference of the lens body, it can be assumed that the axis shift can be preferably prevented since the plunger 30 contacts a portion at which the thickness of the lens body is smaller than the thickness of the other portions of the lens body.

Moreover, a toric intraocular lens generally needs to be adjusted with respect to the position (direction) of the steep meridian in the eyeball immediately after the toric intraocular lens is inserted into the eyeball. However, when the toric intraocular lens according to the embodiments as described above, the angle of rotation of the toric intraocular lens for the adjustment can be smaller and the surgery can be simplified. A reason is that since an incision can reduce the corneal astigmatism in the surgery in practice, the incision is often formed on the side of the steep meridian of the cornea for inserting the toric intraocular lens. In this case, the direction in which the toric intraocular lens is inserted and the direction of the steep meridian of the astigmatism match with each other. Further, it is a common practice to rotate the toric intraocular lens clockwise when the axis of the flat meridian of the toric intraocular lens is adjusted to match with the astigmatism axis. Therefore, when the angle ("θ" in the drawings) between the flat meridian of the lens body and the axis (axis AX) representing the push direction of the plunger 30 is larger than 0° and equal to or smaller than 90°, as described in the present embodiment, the direction of rotation for the position adjustment is the direction in which the toric intraocular lens is rotated clockwise immediately after the toric intraocular lens is inserted into the eyeball of the patient, and the angle of the rotation is an acute angle.

On the other hand, when the axis of the flat meridian is located at the connecting portion of the support portion, the amount of rotation for the adjustment becomes larger than that in case of the acute angle since the angle between the direction to be adjusted and the axis indicated by the toric marks (axis of the flat meridian) is an obtuse angle. When the axis representing the push direction and the axis of the flat meridian are matched with each other, the amount of rotation is assumed to become minimum ideally. However, it can be assumed in practice that the toric intraocular lens is rotated clockwise more than necessary with respect to an ideal position when operations for eliminating viscoelastic material or for establishing the stability of the lens in the eyeball are performed. In this case, since the toric intraocular lens needs to be rotated almost 180° to bring the toric intraocular lens back to the ideal position, there may be a risk at increasing the amount of rotation to the maximum. Thus, it is preferable in practice to arrange that the push direction and the axis of the flat meridian do not match with each other.

In addition, a shift of the axis of the plunger 30 occurs in case of the toric intraocular lenses 110, 140, 150, and 170 as illustrated in FIG. 9. That is, when the toric intraocular lenses 110, 140, 150, and 170 are pushed by the plunger 30, the relation between the position of the toric intraocular lenses 110, 140, 150, and 170 and the position of the plunger 30 in the nozzle body 10 is that the central axis CX of the plunger 30 is shifted from the axis AX as illustrated in FIG. 8B. Referring to FIGS. 6A, 6D, 7A, and 7C, when one of the pair of marks indicating the flat meridian ("EX" in the drawings) of the lens body of the toric intraocular lens, that is one end of the flat meridian is located on the opposite side of the axis (axis DX) that passes through the optical center of the lens body and connects the pair of connecting portions with each other, with respect to the position ("P" in the drawings) at which the tip of the plunger 30 contacts the circumference of the lens body, or is located on the position which overlaps the axis (axis AX) representing the push direction of the plunger 30, and when the angle ("θ" in the drawings) between the flat meridian of the lens body and the axis (axis AX) representing the push direction of the plunger 30 is larger than 90° and equal to or smaller than 180°, it can be said that a shift of the axis of the plunger 30 occurs.

According to verifications of the push load for pushing the toric intraocular lenses 110, 120, 130, 140, 150, 160, 170, and 180 by the plunger 300 when the intraocular lens insertion apparatus 1 is used, the push load has a tendency to increase in relation to the cross section area of the folded toric intraocular lens 2 but the variation of the push load do not become large. For example, in case of a toric intraocular lens with the columnar refractive power of +6.00 D, the variation of the push load is approximately 1N at most and it can be assumed that the variation do not affect the surgery. In addition, according to verifications of the impressions of the pushing by the plunger 30 targeting at the clinicians who have sufficient experiences of intraocular lens insertion surgeries, the results of the verifications show that the clinicians can push the plunger 30 with the same push feelings regardless of the direction of the flat meridian. That is, even when the flat meridian of the toric intraocular lenses 110, 120, 130, 140, 150, 160, 170, and 180 is configured to prevent the shift of the axis of the plunger 30 in the present embodiment, there is not a concern that the push load for pushing the plunger 30 affects the operations in the surgery.

Although the present embodiment is described as above, the configurations of the lens, the insertion member, and the like are not limited to those as described above and various variations may be made within the range that does not lose identity with the technical idea of the above embodiment. For example, it is more preferable that when the tip of the plunger 30 contacts the circumference of the lens body the angle θ is equal to or larger than the angle that achieves that a line extending the flat meridian of the lens body does not intersect the plunger 30, and equal to or smaller than 90°. In addition, in the present embodiment, it is found that the variation of the thickness (edge thickness) of the lens body on its circumference becomes the largest in the middle between the flat meridian direction and the steep meridian direction with respect to the angle around the optical axis, that is at the position where θ=45°. In this case, the edge thickness of the portion which the tip of the plunger 30 contacts reaches a minimal value and further the difference between the minimal value and the edge thicknesses on both ends of the plunger 30 becomes the largest. Therefore, the shift of the position of the tip of the plunger 30 can be prevented effectively. Moreover, there is a possibility that the mark representing the flat meridian direction is placed at a position shifted by +5° or −5° from the flat meridian direction due to a manufacturing error when the toric intraocular lens is manufactured. In light of the above descriptions, the most preferable angle θ as described above is 45°. Preferably, the angle θ is equal to or larger than 10° and equal to or smaller than 80°. More preferably, the angle θ is substantially 45°, that is equal to or larger than 45°−5° and is equal to or smaller than 45°+5°.

In addition, the angle between the axis (DX) connecting the connecting portions with each other and the flat meridian can be 45° in another embodiment. In this case, the shape of the cross section of the toric intraocular lens at a position where the lens is connected with the pair of connecting portions is similar to the shape of the cross section of a single focus intraocular lens having a refractive power similar to the spherical equivalent power of the toric intraocular lens. Therefore, the mechanical characteristics of the toric intraocular lens can be configured similar to the mechanical characteristics of the single focus intraocular lens. Such conformation of the mechanical characteristics means that the stability of the toric intraocular lens in the eyeball can be the same as the stability of the single focus intraocular lens and means that stable surgery performances can be achieved.

FIG. 10A, FIG. 10B, FIG. 11A, FIG. 11B, and FIG. 12 illustrate shapes of the cross sections of the toric intraocular lens along the optical axis thereof. In these figures, the 35 degree direction, the 45 degree direction, and the 55 degree direction are directions on condition that the flat meridian direction is the 0 degree direction and the steep meridian direction is the 90 degree direction. FIG. 10A, FIG. 10B, FIG. 11A, FIG. 11B, and FIG. 12 illustrate examples of the cross sections of the toric intraocular lens having an intraocular principal point refractive power of +20.0 D. In these figures, the horizontal axis represents a distance r (mm) from the optical axis, the vertical axis represents a distance Z (mm) from the vertex of the back surface of the lens, the upper surface represents the front surface (FC) of the lens having an aspherical shape, and the lower surface represents the back surface of the lens which includes the back surface BC of the single focus lens and the toric surface. In addition, the cross sections of the toric surfaces are labelled with "TORIC(LARGE)", "TORIC(MIDDLE)" and "TORIC(SMALL)" in descending order with respect to the columnar refractive power. AS illustrated in these figures, although the shape of the single focus intraocular lens and the shape of the toric intraocular lens are different from each other in the steep meridian direction and in the flat meridian direction, the difference between these shapes in the 45 degree direction is not a difference that may affect the mechanical characteristics. It is desirable that the axis DX is an axis connecting the midpoints of the arcs that contact the connecting portion 2e and the lens body 2a or an axis connecting the midpoints of the arcs on which the supporting portion 2b is connected with connecting portion 2e.

Further, the connecting portion of the toric intraocular lens is configured to contact the circumference of the lens body in a predetermined range, and the connection by the connecting portion in the predetermined range can be achieved without the mechanical characteristics changed adversely. For example, when the connecting portion of the toric intraocular lens contacts the circumference of the lens body in a range from 45°−10° to 45°+10° and the cross sections in the 35 degree direction and in the 55 degree direction are compared, it can be said that the difference between the cross section of the single focus intraocular lens and the cross section of the toric intraocular lens does not affect the mechanical characteristics as is the case with the 45 degree direction. The shape of the optical portion that contacts the connecting portion can be configured such that the above difference becomes an optically meaningful difference. In addition, the axis (DX) connecting the connecting portions of the pair of connecting portions can be arbitrarily set in the predetermined range.

Regarding the direction in which the lens body of the toric intraocular lens is folded in the intraocular lens insertion apparatus, JP-B 5603326 appears to assume that the edge thickness in the 45 degree direction (45 degree direction with respect to the flat meridian) of the toric intraocular lens as above is the same as the edge thickness in the 45 degree direction of the single focus intraocular lens and that the lens body is folded in the 45 degree direction (45 degree direction with respect to the flat meridian) and the folding can be achieved similar to the case of the single focus intraocular lens which the toric intraocular lens is manufacture based on. In the present embodiment on the other hand, since the push load is related more or less to the cross section area of the folded lens body as described above, the lens body is folded in a direction that the cross section area can be relatively smaller, that is in a direction that the steep meridian is folded (with the flat meridian as the center), the push load can be smaller and the possibility that the lens and the insertion member may be damaged can be decreased. In addition, the shift of the axis of the plunger can be prevented when the user performs the push operation in the present embodiment. As a result, a more secure and more stable push operations can be provided.

Further, when the connecting portion of the toric intraocular lens is configured to contact the circumference of the lens body in the predetermined range, the mechanical characteristics can be preferably maintained and the position of the flat meridian can be adjusted in the range in which the connecting portion and the circumference of the lens body contact each other.

A variation of the above embodiment can be provided such that the edge thickness in the 45 degree direction with respect to the flat meridian for the toric intraocular lens is not the same as the edge thickness of the single focus intraocular lens, considering that the edge portion of the lens body in the 45 degree direction is a portion overlapping with the connecting portion for connecting with the support portion. Alternatively, as disclosed in WO2015/136997 A1, optical characteristics can be added or the handling of the lens can be improved by varying the edge of the lens body around the optical axis in a non-sinusoidal manner to achieve that the edge thickness in the 45 degree direction with respect to the flat meridian differs from the edge thickness of the single focus intraocular lens the shape of which is the base shape of the toric intraocular lens. Although it can be assumed that the edge of the lens body is a mechanical edge that is the edge surface of the shape itself of the lens body or an optical edge that is the boundary between the optical portion and the non-optical portion, namely corresponding to the periphery of the portion effectively functioning as a lens, the edge of the lens body is assumed to be the optical edge in the present embodiment.

Additionally, a variation of the above embodiment can be provided such that the flat meridian of the intraocular lens overlaps the line connecting the tip of each support portion of the pair of support portions in the state in which the intraocular lens is compressed down to from $\phi 9$ mm to $\phi 11$ mm in the eyeball. Since an intraocular lens is generally fixed on the side of the retina with respect to the pupil, an operator can observe the lens only in an area that is smaller than the size defined by the pupil diameter when the lens is inserted into the eyeball. Therefore, the operator may find it difficult to identify the position of the tip of the support portion. However, since the pair of marks representing the flat meridian are provided in an area that is smaller than the size defined by the pupil diameter and the tips of the support portions are arranged on the line extending the pair of marks in the present embodiment, the operator can precisely identify the positions of the tips of the support portions.

For example, when an conventional intraocular lens is inserted into an eyeball and the posterior capsule wrinkles, the operator finds it difficult to identify the cause because the operator can do nothing but guess the position of the tip of the support portion from the position of the root part of the support portion and cannot determine the area in which the support portion is located. However, the operator can precisely determine the area in which the support portion is located in the present embodiment. Therefore, the operator can examine the relation between the posture of the intraocular lens and the wrinkles. In addition, even when a crack occurs in the crystalline capsule which the intraocular lens is fixed to, the operator can easily adjust the tip of the support portion not to be located toward the crack. Further, when the toric intraocular lens is a one-piece type lens in the present embodiment and the toric intraocular lens is rotated in the eyeball, the tip of the support portion contacts the crystalline capsule. Thus, the arrangement that the axis connecting the tips of the support portions of the pair of support portions overlaps the axis connecting the marks can improve the stability of the movement of the lens in the eyeball.

Moreover, when the intraocular lens as described above is manufactured, the relation between the position of the support portion and the position of the mark in the state that the intraocular lens is compressed in the eyeball can be determined by placing an intraocular lens of the same size, which is previously manufactured, in a holder etc. with the inner diameter of from $\phi 9$ mm to $\phi 11$ mm. Therefore, the intraocular lens can be manufactured based on such information. In a case where the deformation of the support portion due to the compression in the eyeball is not significant, the intraocular lens can be manufactured as illustrated in FIG. 7D such that the flat meridian overlaps the line connecting the tips of the support portions of the pair of support portions in the state of the initial shape of the intraocular lens (in the state that the intraocular lens is not compressed).

REFERENCE SIGNS LIST 1 intraocular lens insertion apparatus
2, 110, 120, 130, 140, 150, 160, 170, 180 toric intraocular lens
2a, 110a, 120a, 130a, 140a, 150a, 160a, 170a, 180a lens body
2b, 110b, 120b, 130b, 140b, 150b, 160b, 170b, 180b support portion
2d, 110d, 120d, 130d, 140d, 150d, 160d, 170d, 180d mark
2e, 110e, 120e, 130e, 140e, 150e, 160e, 170e, 180e connecting portion
10 nozzle body
100 insertion tube

What is claimed is:

1. A toric intraocular lens comprising a lens body having a flat meridian and a steep meridian, a pair of support portions for positioning the lens body in an eyeball, and connecting portions for connecting the lens body and the support portions,
   wherein the toric intraocular lens is housed in an intraocular lens insertion apparatus that comprises a tubular apparatus body having an insertion tube at a distal end of the apparatus body for inserting the toric intraocular lens into the eyeball and a plunger for moving the toric intraocular lens to a distal end of the insertion tube, each of the connecting portions is arranged at a position where the connecting portions face each other across a center of an optical axis of the lens body, one end of the flat meridian of the lens body is located at a position opposite to a position, with respect to an axis that passes through the center of the optical axis and connects the connecting portions with each other, at which a tip of the plunger contacts a circumference of the lens body, and an angle θ between the flat meridian of the lens body and an axis of the plunger along which the toric intraocular lens is pushed by the plunger is larger than 0° and equal to or smaller than 90°.

2. The toric intraocular lens according to claim 1, wherein when the tip of the plunger contacts the circumference of the lens body, the angle θ is equal to or larger than an angle that achieves that a line extending the flat meridian does not intersect the plunger and equal to or smaller than 90°.

3. The toric intraocular lens according to claim 1, wherein the angle θ is larger than 10° and smaller than 80°.

4. The toric intraocular lens according to claim 1, wherein the angle θ is substantially equal to 45°.

5. The toric intraocular lens according to claim 1, wherein a mark is provided for each end of the flat meridian on the lens body.

6. The toric intraocular lens according to claim 5, wherein a tip of the support portion is located on an axis that connects the marks with each other.

7. The toric intraocular lens according to claim 1, wherein an angle between the axis that connects the connecting portions with each other and the flat meridian is from 45°−10° to 45°+10°.

8. An intraocular lens insertion apparatus, wherein the toric intraocular lens according to claim 1 is housed in advance in a housing member for housing the toric intraocular lens of the intraocular lens insertion apparatus.

* * * * *